(12) United States Patent
Williams

(10) Patent No.: US 9,561,136 B2
(45) Date of Patent: Feb. 7, 2017

(54) BANDAGE

(71) Applicant: Gregory Troy Williams, Calgary (CA)

(72) Inventor: Gregory Troy Williams, Calgary (CA)

( * ) Notice: Subject to any disclaimer, the term of this patent is extended or adjusted under 35 U.S.C. 154(b) by 250 days.

(21) Appl. No.: 14/209,812

(22) Filed: Mar. 13, 2014

(65) Prior Publication Data

US 2015/0257937 A1    Sep. 17, 2015

(51) Int. Cl.
*A61F 13/00* (2006.01)
*A61F 13/02* (2006.01)
*A61F 15/00* (2006.01)

(52) U.S. Cl.
CPC ....... *A61F 13/0243* (2013.01); *A61F 13/0206* (2013.01); *A61F 13/0226* (2013.01); *A61F 15/008* (2013.01); *A61F 2013/00165* (2013.01); *A61F 2013/00217* (2013.01)

(58) Field of Classification Search
CPC .... A61F 13/0203; A61F 13/06; A61F 15/008; A61F 13/00051; A61F 13/068; A61F 13/069; A61F 13/101; A61F 2013/00165; A61F 13/00034; A61F 13/00046; A61F 13/02; A61F 13/0226; A61F 13/0243; A61F 2013/00217
USPC ...................... 602/41–54; 128/888, 889, 890
See application file for complete search history.

(56) References Cited

U.S. PATENT DOCUMENTS

| | | | |
|---|---|---|---|
| 828,311 A * | 8/1906 | Heidemann | A61F 15/008 128/888 |
| 2,785,677 A | 3/1957 | Stumpf | |
| 3,234,941 A * | 2/1966 | Tucker | A61F 13/02 128/888 |
| 4,005,709 A | 2/1977 | Laerdal | |
| 4,333,471 A * | 6/1982 | Nakai | A61F 13/145 128/890 |
| 4,667,666 A | 5/1987 | Fryslie | |
| 4,754,750 A * | 7/1988 | Imonti | A61F 15/008 128/888 |
| 5,170,781 A | 12/1992 | Loomis | |
| 6,096,943 A | 8/2000 | Maiwald | |
| 6,274,786 B1 * | 8/2001 | Heller | A61F 13/148 128/888 |
| 6,274,787 B1 | 8/2001 | Downing | |
| 6,320,093 B1 | 11/2001 | Augustine | |
| 6,570,050 B2 | 5/2003 | Augustine | |

(Continued)

FOREIGN PATENT DOCUMENTS

| | | |
|---|---|---|
| CA | 1081928 | 7/1980 |
| CA | 2255627 | 12/1997 |

(Continued)

*Primary Examiner* — Michael Brown
(74) *Attorney, Agent, or Firm* — Richard D. Okimaw

(57) ABSTRACT

A bandage for applying to and protecting a wound or the like comprises generally of a central cone piece with a plurality of attached legs. In a second embodiment of the present invention, the bandage comprises generally a substantially circular mid-piece with a center region; a proximal first flexible strip end; and a distal second flexible strip end. The substantially circular mid-piece with a center region is perforated along a radius from about the center region to a circumference of the substantially circular mid-piece and the proximal first flexible strip end is perforated longitudinally along a midline from about an end of the proximal first flexible strip to the circumference of the substantially circular mid-piece.

12 Claims, 4 Drawing Sheets

(56) References Cited

U.S. PATENT DOCUMENTS

| | | |
|---|---|---|
| 7,265,256 B2 | 9/2007 | Artenstein |
| 8,237,008 B1 | 8/2012 | Alessandrini |
| 2003/0109816 A1 | 6/2003 | Lachenbruch et al. |
| 2005/0033212 A1* | 2/2005 | Scheinberg ......... A61F 13/0203 602/43 |
| 2009/0069737 A1 | 3/2009 | Stapley et al. |
| 2012/0179127 A1 | 7/2012 | Riesinger |
| 2012/0277648 A1 | 11/2012 | Kendall |
| 2013/0226061 A1 | 8/2013 | Dickson |

FOREIGN PATENT DOCUMENTS

| | | |
|---|---|---|
| CA | 2283997 | 10/1998 |
| CA | 2660036 | 2/2008 |
| WO | 2006036679 | 4/2006 |
| WO | 2011141454 | 5/2011 |

* cited by examiner

BANDAGE

BACKGROUND OF THE INVENTION

1. Field of Invention

The present invention relates to the field of wound care. More specifically, the present invention relates to adhesive bandages and methods for protecting a wound with a bandage.

2. Description of Related Art

Adhesive bandages are used to protect wounds from friction, bacteria, damage and dirt in order to facilitate the healing process. Typically, an adhesive bandage lays flat on the wounds and is covered by a woven plastic or latex strip that contains an absorbent dressing that may or may not be medicated with an antibacterial or antiseptic compound. The bandage is usually applied such that the dressing covers the wound and the woven plastic or latex strip is adhered to the skin thereby holding the bandage in place over the wound.

The adhesive bandage is well known in the prior art. While most bandages lay flat against a wound, there have been various attempts to create a raised area above the wound so that the wound is not irritated by the bandage covering. For example, U.S. Pat. No. 2,785,677 to Stumpf, U.S. Pat. No. 4,667,666 to Fryslie, U.S. Pat. No. 5,170,781 to Loomis, U.S. Pat. No. 6,096,943 to Maiwald, U.S. Pat. No. 7,265,256 to Arenstein and U.S. Pat. No. 8,237,008 to Alessandrini all disclose a bandage with a raised area with shapes ranging from circular, semi-circular to rectangular. However, the application of pressure against these raised areas results in the bandage pressing up against the wound. Further, as the raised areas are a permanent part of the bandage design, the bandages are unable to be easily transported and stored. The present invention is distinguishable from the prior art in that it creates a raised cone, which is significantly more difficult to press against the wound based on the strength of the cone design. Further, the cone is created at the time of bandage application and not manufacture, thus allowing the bandages to be shipped and stored in flat position.

While U.S. Pat. No. 6,570,050 to Augustine et.al. discloses a semi cone like raised area above the wound, the adhesive material of the bandage is limited to a round shape that does not allow for the bandage to grasp "hard to apply" body locations such as the fingers or other appendages. The present invention is distinguishable from '050 to Augustine in that it may be applied as a flat bandage or may be applied in the cone shape above the wound. Further, the bandage has attached legs that may be used to grip the skin and body parts around the wound location.

SUMMARY OF THE INVENTION

It is the object of the present invention to address several challenges in previous attempts to apply bandages and protect wounds. In one embodiment of the present invention, a bandage for applying to and protecting a wound or the like is disclosed. The bandage is comprised generally of a central cone piece with a plurality of attached legs. In a second embodiment of the present invention, the bandage comprises generally a substantially circular mid-piece with a center region; a proximal first flexible strip end; and a distal second flexible strip end. The substantially circular mid-piece with a center region is perforated along a radius from about the center region to a circumference of the substantially circular mid-piece and the proximal first flexible strip end is perforated longitudinally along a midline from about an end of the proximal first flexible strip to the circumference of the substantially circular mid-piece.

In a third embodiment of the present invention, a method of applying and protecting a wound with a bandage is disclosed. The method comprises generally applying a bandage with a central cone piece with a plurality of attached legs to the wound or the like.

The present invention can be used to protect small burns, cushion blisters, cover stitches, or to hold cream or salve over wound. The bandage has the advantage of either being applied in a flat position applied such that the cone is twisted into place to create the raised area above the wound. This is particularly advantageous as it allows the manufacturer to ship and the user to store a potential three-dimensional bandage in the flat position. Further, the bandage can be used to cover not just a wound but also protect and cover anything sticking out of the wound such as a nail, wood, etc. until it can be safely removed.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
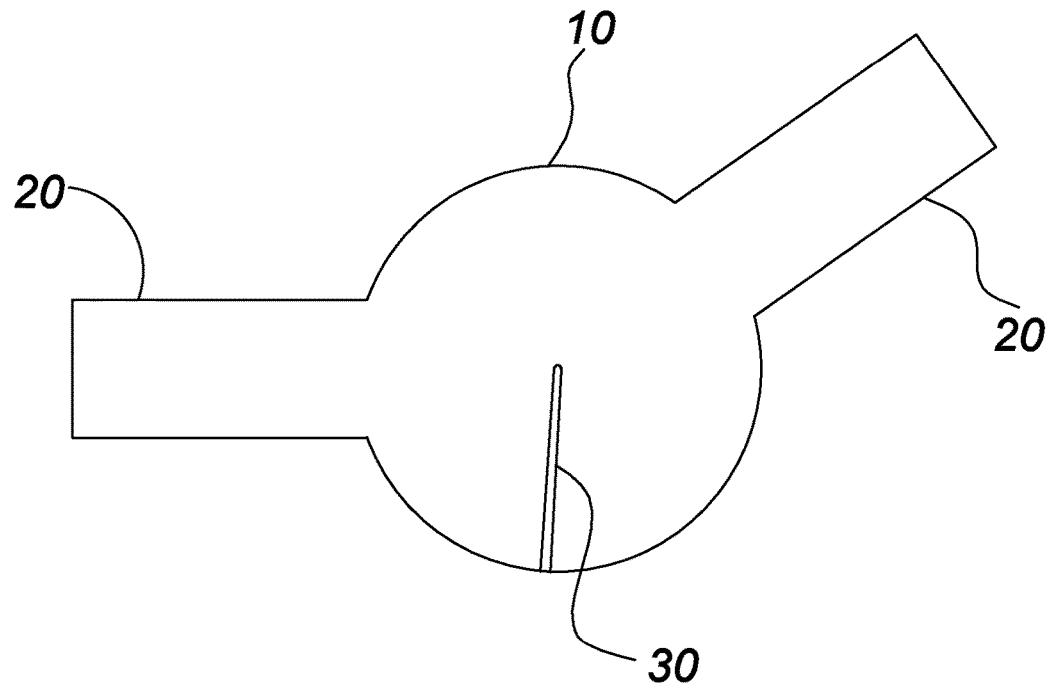
FIG. 1 is a top view of one embodiment of the present invention before twisting the cone into place.
Figure 2:
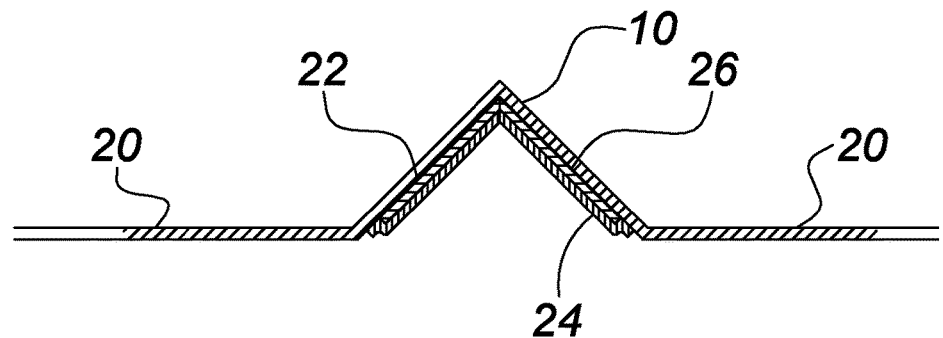
FIG. 2 is a cross sectional view of one embodiment of the present invention after twisting the cone into place.

Turning to FIG. 1, a top view of the present invention shows the central cone piece 10 attached to legs 20 with the cone mid-line 30. As shown in the side view of FIG. 2, the cone piece 10 is twisted into the cone position by overlapping the central cone piece 10 about the cone mid-line 30. In the preferred embodiment, the cone piece 10 and legs 20 are formed of a thin flexible strip of material having a top outer layer 22 and a bottom inner layer 24. The outer layer 22 may be formed of any suitable material such as, by way of non-limiting example, woven fabric, plastic or latex as are commonly known in the art. The bottom layer 24 may be formed of an absorbent non-adhesive layer to prevent wounds and the like from adhering thereto as are commonly known in the art. As illustrated, the inner layer 24 may be applied to the cone piece 10 only. An adhesive may be attached to the bottom of the outer layer along the legs 20 for securing the bandage to a users skin. In an alternative embodiment, a rigid breathable middle layer 26 such as, by way of non-limiting example, plastic, woven fabric or latex is part of the central cone piece 10 and is located between the top out layer and bottom inner layer of the thin flexible strip of material. The central cone piece 10 may be attached to a plurality of legs 20, with the preferred embodiments being two or three legs.

Figure 3:
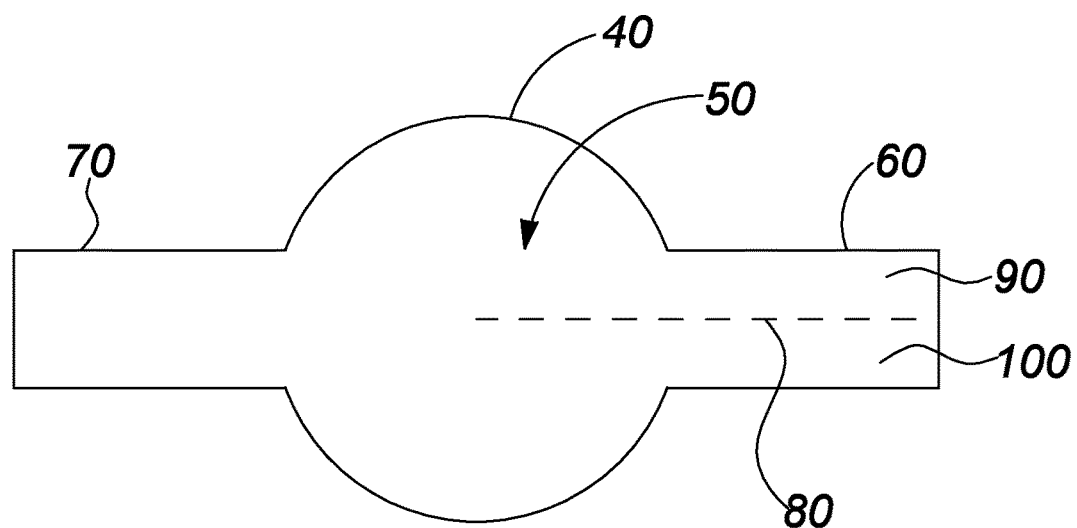
FIG. 3 is a top view of an alternative embodiment of the present invention before twisting the cone into place
Figure 4:
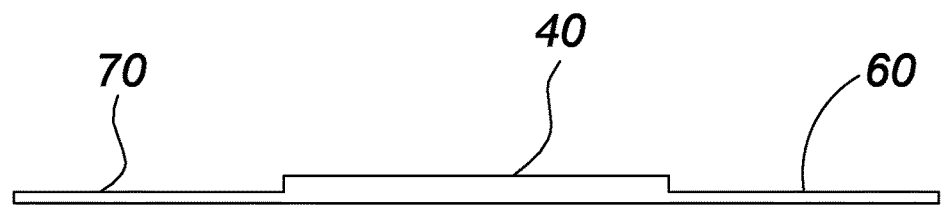
FIG. 4 is a side view of an alternative embodiment of the present invention before twisting the cone into place
Figure 6:
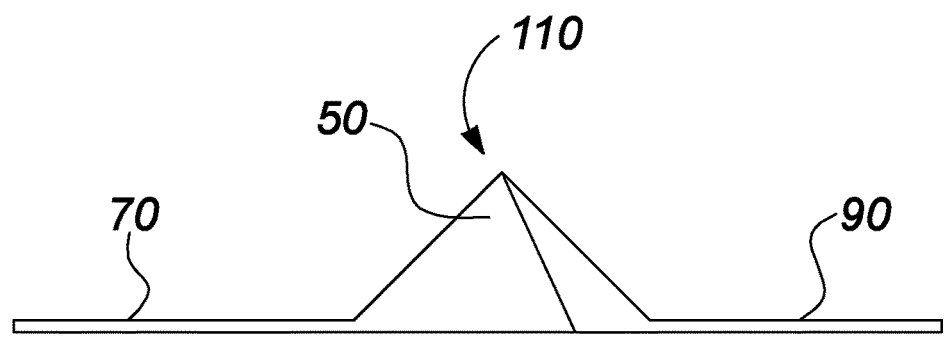
FIG. 6 is a side view of an alternative embodiment of the present invention after twisting the cone into place.

Turning to FIG. 3, an alternative embodiment of the present invention is shown generally to comprise a thin flexible strip of material that has a top outer layer and a bottom inner layer. The thin flexible strip includes a substantially circular mid-piece 40 with a center region 50. The circular mid-piece is connected with a proximal first flexible strip end 60 and a distal second flexible strip end 70. The circular mid-piece 40 has a perforation 80 that runs along the radius of the circular mid-piece 40. The perforation 80 extends down the proximal first flexible strip end 60 longitudinally along the mid-line of the proximal first flexible strip end 60 and meets with the perforation of the circular mid-piece 40. FIG. 4 shows the thin flexible strip of material from the side view prior to forming the central cone 110 shown in FIG. 6.

Figure 5:
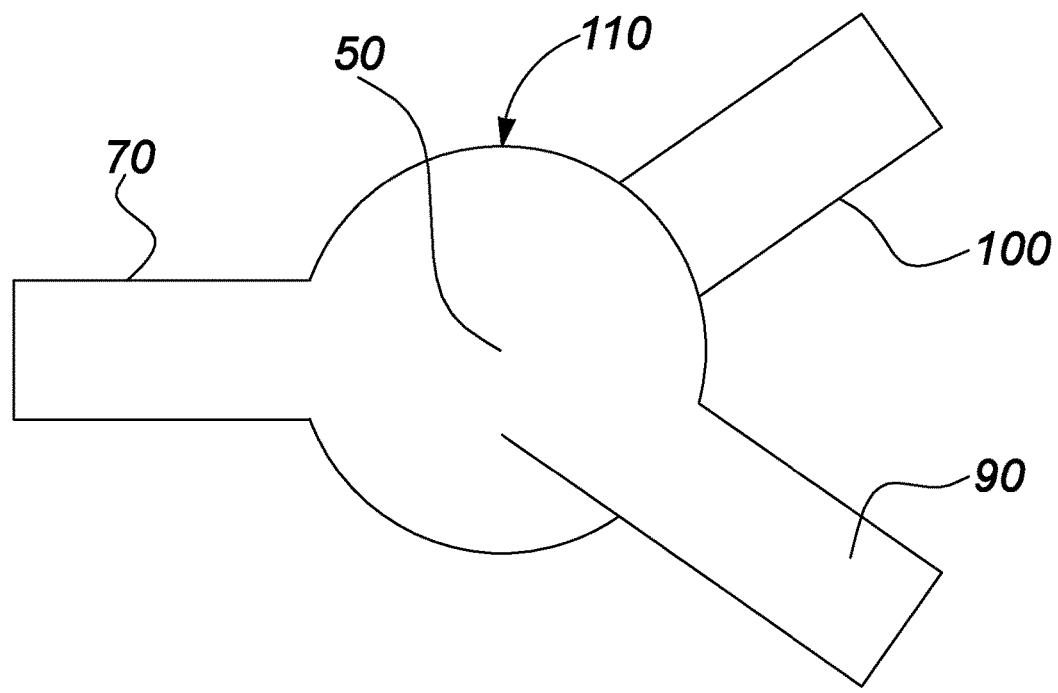
FIG. 5 is a top view of an alternative embodiment of the present invention after twisting the cone into place.

As shown in FIGS. 3 and 4, the circular mid-piece 40 with a center region 50 is separated along its perforated radius from about the center region to about the circumference and co-linear with the perforated mid-line 80 of at least one flexible strip end and the flexible strip end is separated longitudinally along its perforated midline 80 to about the circumference of the substantially circular mid-piece 40 in order to provide a first-half of the flexible strip and a second-half of the flexible strip end. The separated circular mid-piece 40 is twisted to form a central cone piece 110 with a plurality of attached legs shown in FIGS. 5 and 6 as legs 90 and 100.

In the preferred embodiment, the circular mid-piece 40 and flexible strip ends 60 and 70 make up a thin flexible strip of material, with the material having a top outer layer 22 and a bottom inner layer 24 as set out above. A rigid breathable middle layer 26 may be attached to the top outer layer and an adhesive layer may be attached to the bottom of the inner layer of the thin flexible strip of material. In an alternative embodiment, a rigid breathable material such as, by way of non-limiting example, plastic, woven fabric or latex is part of the central cone piece 110 and is located between the top out layer and bottom inner layer of the thin flexible strip of material.

Figure 7:
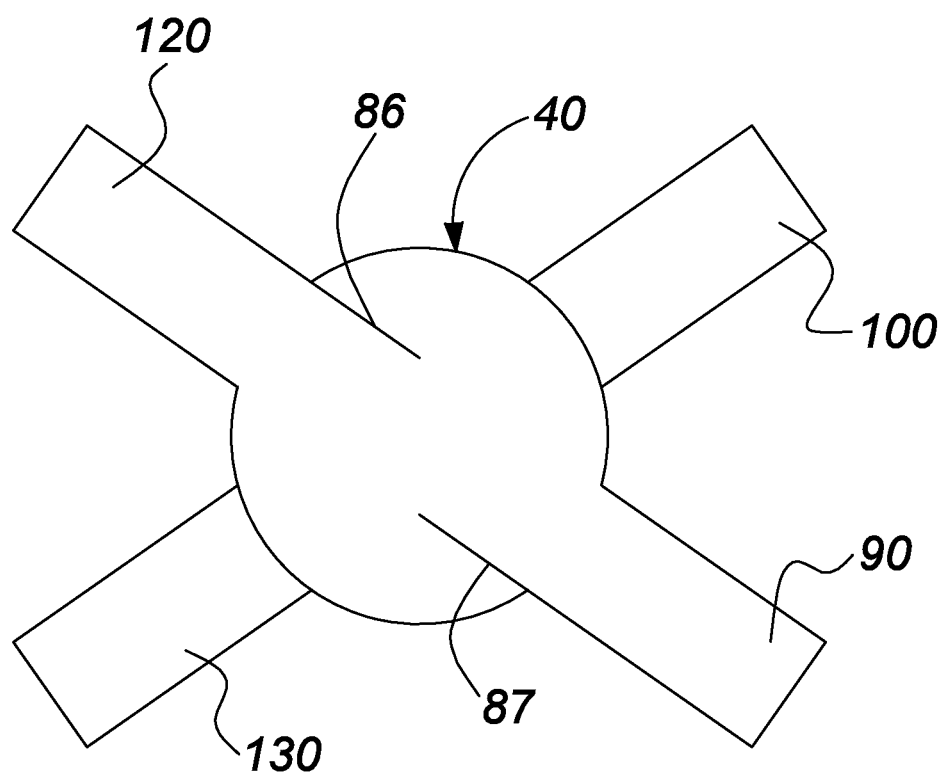
FIG. 7 is a top view of an alternative embodiment of the present invention before the cone is twisted into place

An alternative embodiment of the present invention is shown in FIG. 7 wherein both flexible strip ends are perforated in the same manner as described above such that the circular mid-piece has a first cone mid-line 86 and a second cone mid-line 87. The flexible strip ends are separated longitudinally along its perforated midlines to about the circumference of the substantially circular mid-piece 40 in order to provide a first-half of the flexible strip and a second-half of the flexible strip end. The separated circular mid-piece 40 is twisted to form a central cone piece 110 with a plurality of attached legs shown in FIG. 7 as legs 90, 100, 120 and 130.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the method (and components of the individual operating components of the method) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections might be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A bandage for applying to and protecting a wound or the like, comprising:
   a central cone piece; and
   a plurality of attached legs extending from said central cone piece,
   wherein the central cone piece and the plurality of attached legs comprise:
      a thin flexible strip of material having a top outer layer and a bottom inner layer;
      a latex or cloth layer attached to the top outer layer of the thin flexible strip of material;
      an adhesive layer attached to the bottom inner layer of the thin flexible strip of material; and
      a rigid breathable material in the central cone piece, wherein the rigid breathable material is located between the top outer layer of the thin flexible strip of material and the bottom inner layer of the thin flexible strip of material.

2. The bandage of claim 1, wherein the bandage with a central cone piece has two attached legs.

3. The bandage of claim 1, wherein the bandage with a central cone piece has three attached legs.

4. A bandage for applying to and protecting a wound or the like, comprising:
   a thin flexible strip of material having a top outer layer and a bottom inner layer, wherein the thin flexible strip of material includes:
      a substantially circular mid-piece with a center region;
      a proximal first flexible strip end; and
      a distal second flexible strip end,
   wherein the substantially circular mid-piece with a center region is perforated along a radius from about the center region to a circumference of the substantially circular mid-piece, and
   wherein the proximal first flexible strip end is perforated longitudinally along a midline from about an end of the proximal first flexible strip to the circumference of the substantially circular mid-piece.

5. The bandage of claim 4, further comprising a latex or cloth layer attached to the top outer layer of the thin flexible strip of material.

6. The bandage of claim 5, further comprising an adhesive layer attached to the bottom inner layer of the thin flexible strip of material.

7. The bandage of claim 6, further comprising a rigid breathable material in the center region of the substantially circular mid-piece, wherein the rigid breathable material is located between the top outer layer of the thin flexible strip of material and the bottom inner layer of the thin flexible strip of material.

8. The bandage of claim 7, wherein the substantially circular mid-piece with a center region is separated along its perforated radius from about the center region to about the circumference, and wherein the separated circular mid-piece is twisted to form a central cone piece with two attached legs.

9. The bandage of claim 7, wherein the substantially circular mid-piece with a center region is separated along its perforated radius from about the center region to about the circumference and co-linear with the perforated mid-line of at least one flexible strip end, and wherein the flexible strip end is separated longitudinally along its perforated midline to about the circumference of the substantially circular mid-piece, to provide a first-half of the flexible strip and a second-half of the flexible strip end, wherein the separated circular mid-piece is twisted to form a central cone piece with a plurality of attached legs.

10. A method of applying and protecting a wound or the like with a bandage, the method comprising:
   applying a bandage with a central cone piece with a plurality of attached legs to the wound or the like, wherein the central cone piece with the plurality of attached legs comprises:
   a thin flexible strip of material having a top outer layer and a bottom inner layer;
   a latex or cloth layer attached to the top outer layer of the thin flexible strip of material;
   an adhesive layer attached to the bottom inner layer of the thin flexible strip of material; and
   a rigid breathable material in the central cone piece, wherein the rigid breathable material is located between the top outer layer of the thin flexible strip of material and the bottom inner layer of the thin flexible strip of material.

11. The method of claim 10, wherein the bandage with a central cone piece has two attached legs.

12. The method of claim 10, wherein the bandage with a central cone piece has three attached legs.

* * * * *